United States Patent
Araki

(10) Patent No.: US 10,036,719 B2
(45) Date of Patent: Jul. 31, 2018

(54) GAS SENSOR

(71) Applicant: DENSO CORPORATION, Kariya, Aichi-pref. (JP)

(72) Inventor: Takashi Araki, Nagoya (JP)

(73) Assignee: DENSO CORPORATION, Kariya (JP)

( * ) Notice: Subject to any disclaimer, the term of this patent is extended or adjusted under 35 U.S.C. 154(b) by 92 days.

(21) Appl. No.: 14/443,750

(22) PCT Filed: Nov. 18, 2013

(86) PCT No.: PCT/JP2013/081018
§ 371 (c)(1),
(2) Date: May 19, 2015

(87) PCT Pub. No.: WO2014/080860
PCT Pub. Date: May 30, 2014

(65) Prior Publication Data
US 2015/0276654 A1  Oct. 1, 2015

(30) Foreign Application Priority Data

Nov. 20, 2012 (JP) .................................. 2012-254229
Sep. 25, 2013 (JP) .................................. 2013-198540

(51) Int. Cl.
G01N 27/403 (2006.01)
G01N 27/407 (2006.01)

(52) U.S. Cl.
CPC ........ *G01N 27/403* (2013.01); *G01N 27/4077* (2013.01)

(58) Field of Classification Search
CPC .......... G01N 27/4077; G01N 33/0009; G01M 15/102
See application file for complete search history.

(56) References Cited

U.S. PATENT DOCUMENTS 6,279,376 B1 * 8/2001 Yamada ............. G01N 27/4077
73/23.2
2009/0020425 A1   1/2009 Yamada
2011/0283774 A1  11/2011 Sekiya et al.

FOREIGN PATENT DOCUMENTS

JP    62-108862    7/1987
JP    2003-043002  2/2003
(Continued)

OTHER PUBLICATIONS

International Search Report for PCT/JP2013/081018 dated Feb. 18, 2014, five pages.
(Continued)

*Primary Examiner* — J. Christopher Ball
(74) *Attorney, Agent, or Firm* — Nixon & Vanderhye P.C.

(57) ABSTRACT

A gas sensor 1 includes a sensor element 2, a housing 13 and an element cover 3. Gas introduction parts 271 are provided in the distal end portion 201 of the sensor element 2. The element cover 3 includes an inner cover 4 and an outer cover 5. The outer cover 5 is provided with outer introduction openings 52. The inner cover 4 is provided with inner introduction openings 42 and louver parts 44 each of which is folded from the end portion 421 at the axial distal end side X1 of the inner introduction opening 42 to the inside of the inner cover 4, and is formed toward the axial proximal end side X2. When the louver part 44 is projected onto the same plane as the inner introduction opening 42, a pair of lateral end edges of the louver part 44 are formed in approximately parallel to the louver forming direction heading from the base side to the distal end side of the louver part 44 and in a roughly linear shape.

8 Claims, 15 Drawing Sheets

(56) References Cited

FOREIGN PATENT DOCUMENTS

| JP | 2009-025076 | 2/2009 |
| JP | 2010-164359 | 7/2010 |
| JP | 2012-002805 | 1/2012 |
| JP | 2012-021895 | 2/2012 |

OTHER PUBLICATIONS

International Preliminary Report on Patentability dated Jun. 4, 2015 issued in corresponding International Application No. PCT/JP2013/081018.
Office Action (2 pages) dated May 19, 2015, issued in corresponding Japanese Application No. 2013-198540 and English translation (3 pages).

* cited by examiner

GAS SENSOR

This application is the U.S. national phase of International Application No. PCT/JP2013/081018 filed 18 Nov. 2013 which designated the U.S. and claims priority to JP Patent Application No. 2012-254229 filed 20 Nov. 2012 and JP Patent Application No. 2013-198540 filed 25 Sep. 2013, the entire contents of each of which are hereby incorporated by reference.

TECHNICAL FIELD

The present invention relates to a gas sensor for detecting a specific gas concentration in a measurement gas.

BACKGROUND ART

Previously, there is known a gas sensor which is provided in an exhaust pipe or the like of an internal combustion engine of an automobile for detecting a specific gas concentration in an exhaust gas as a measurement gas. As the gas sensor, there is the one that includes a sensor element which detects a specific gas concentration in a measurement gas, a housing holding the sensor element inserted thereinto, and an element cover disposed at the distal end side of the housing, for example.

For example, patent literature 1 discloses a gas sensor provided with a double-structured element cover which includes an inner cover covering the distal end portion of a sensor element provided with a gas introduction part for preventing the sensor element from being flooded, and an outer cover disposed outside the inner cover. The outer cover of this gas sensor is provided with outer introduction openings for introducing the measurement gas into the outer cover. Also, the inner cover is provided with inner introduction openings for introducing the measurement gas into the inner cover, and a louver part which is folded from the end at the axial distal side of each inner introduction opening to the inside of the inner cover and is formed toward the axial proximal end side.

CITATION LIST

Patent Literature

[PTL1] Japanese Patent Application Laid-open No. 2009-25076

SUMMARY OF INVENTION

Technical Problem

Incidentally, in a multi-cylinder internal combustion engine, there occurs a cylinder-to-cylinder variation in an air-fuel ratio (cylinder-to-cylinder imbalance) due to a cylinder-to-cylinder variation in fuel injection amount. In recent years, it is required to accurately detect the cylinder-to-cylinder imbalance of an internal combustion engine in a gas sensor to perform air-fuel ratio control for each cylinder by a further exhaust gas regulations and fuel economy regulations. Accordingly, it is necessary to further increase the responsiveness of the gas sensor with change of the air-fuel ratio of each cylinder in order to further correctly detect a change of the output value (air-fuel ratio: A/F) of the gas sensor used as an index of the cylinder-to-cylinder imbalance. Specifically, other than increasing the responsiveness of the gas sensor itself for the A/F change, particularly in the element cover for covering the sensor element, it is crucial to suppress the measurement gases which are different in A/F and discharged successively from the respective cylinders from being mixed before reaching a detection part (the part for detecting a measurement gas) of the sensor element, in addition to causing the measurement gases to reach the gas detection part of the sensor element rapidly through a short distance.

However, in the gas sensor of the above patent literature 1, as shown in FIGS. 19 and 20 where the louver part 94 is projected onto the same plane (plane h) as the inner introduction opening, a pair of the lateral end edges 943a and 944a of the louver part 94 are inclined inwardly to the direction heading from the base toward the distal end of the louver part 94 (the louver forming direction v). The angle b1 and b2 between the base side end edge 942a and the pair of the lateral end edges 943a and 944a of the louver part 94 are smaller than 90 degrees. Accordingly, as shown in FIG. 21, when a measurement gas g flows from the inner introduction opening 92 into the inner cover along the surface of the louver part 94, part of the measurement gas g leaks to both sides from the lateral end portions 943 and 944, and flows into the inner cover.

Accordingly, there may occur a difficulty in the measurement gas g being introduced into the inner cover to reach the gas introduction part of the sensor element, or the distance to the gas introduction part becomes long, or it may mix with a measurement gas having flowed from another inner introduction opening. This may lower the detection accuracy of the cylinder-to-cylinder imbalance of the internal combustion engine, causing the responsiveness of the gas sensor for detecting the cylinder-to-cylinder imbalance to be degraded.

The present invention, which has been made in view of such a background, aims to provide a gas sensor that is capable of increasing the detection accuracy of the cylinder-to-cylinder imbalance of an internal combustion engine, and is excellent in responsiveness for detecting the cylinder-to-cylinder imbalance.

Solution to Problem

One aspect of the present invention is in a gas sensor including:
a sensor element for detecting a specific gas concentration in a measurement gas;
a housing in which the sensor element is inserted; and an element cover disposed at an axial distal end side of the housing; wherein
a gas introduction part is provided in a distal end portion of the sensor element for introducing therein the measurement gas, the element cover includes an inner cover disposed so as to cover the distal end portion of the sensor element and an outer cover disposed outside the inner cover,
the outer cover is provided with an outer introduction opening for introducing the measurement gas into the outer cover,
the inner cover is provided with an inner introduction opening for introducing the measurement gas into the inner cover, and a louver part which is folded from an end portion at an axial distal end side of the inner introduction opening to the inside of the inner cover and is formed toward an axial proximal end side, and
when the louver part is projected onto a same plane as the inner introduction opening, a pair of lateral end edges of the louver part are formed in an approximately linear shape so as to be approximately parallel or inclined outwardly to a louver part forming direction heading from a base side to a distal end side of the louver part.

Advantageous Effect of the Invention

In the above gas sensor, the inner cover is provided with the inner introduction opening, and the louver part which is folded from the end portion at the axial distal end side of the inner introduction opening to the inside of the inner cover and is formed toward the axial proximal end side. When the louver part is projected onto the same plane as the inner introduction opening, the pair of lateral end edges of the louver part are formed in an approximately linear shape so as to be approximately parallel or inclined outwardly to the louver part forming direction heading from the base side to the distal end side of the louver part (see later-explained FIGS. 5, 6 and 12).

Accordingly, when the measurement gas introduced into the outer cover (between the outer cover and the inner cover) from the outer introduction opening part flows from the inner introduction opening into the inner cover, the measurement gas easily flows from the based side to the distal end side of the louver part along the surface of the louver part. Further, part of the measurement gas can be suppressed from leaking from the lateral end portions of the louver part to both sides, and flowing into the inner cover. That is, it is possible to increase the percentage of the flow amount of the measurement gas flowing in through the distal end portion of the louver part (see later-explained FIGS. 7 and 13).

As a result, it becomes easy to cause the measurement gas to flow from the inner introduction opening in a desired direction within the inner cover through the louver part, so that the measurement gas can be caused to reach the gas introduction part of the sensor element rapidly through a distance as short as possible. Further, it is possible to cause the measurement gas to reach the gas introduction part of the sensor element without mixing a measurement gas having flowed in through another inner introduction opening. Further, it is possible to suppress the measurement gases of the respective cylinders from mixing with one another, and to cause the measurement gases of the respective cylinders to reach the gas introduction part of the sensor element in succession.

As a result, the responsiveness of the gas sensor can be increased, and the output value (air-fuel ratio: A/F, for example) used as an index of the cylinder-to-cylinder imbalance of an internal combustion engine can be detected more accurately. Further, the detection accuracy of the cylinder-to-cylinder imbalance of an internal combustion engine can be increased.

Thus, it is possible to provide a gas sensor which is capable of increasing the detection accuracy of the cylinder-to-cylinder imbalance of an internal combustion engine and is excellent in the responsiveness for detecting the cylinder-to-cylinder imbalance.

DESCRIPTION OF EMBODIMENTS

Figure 1:
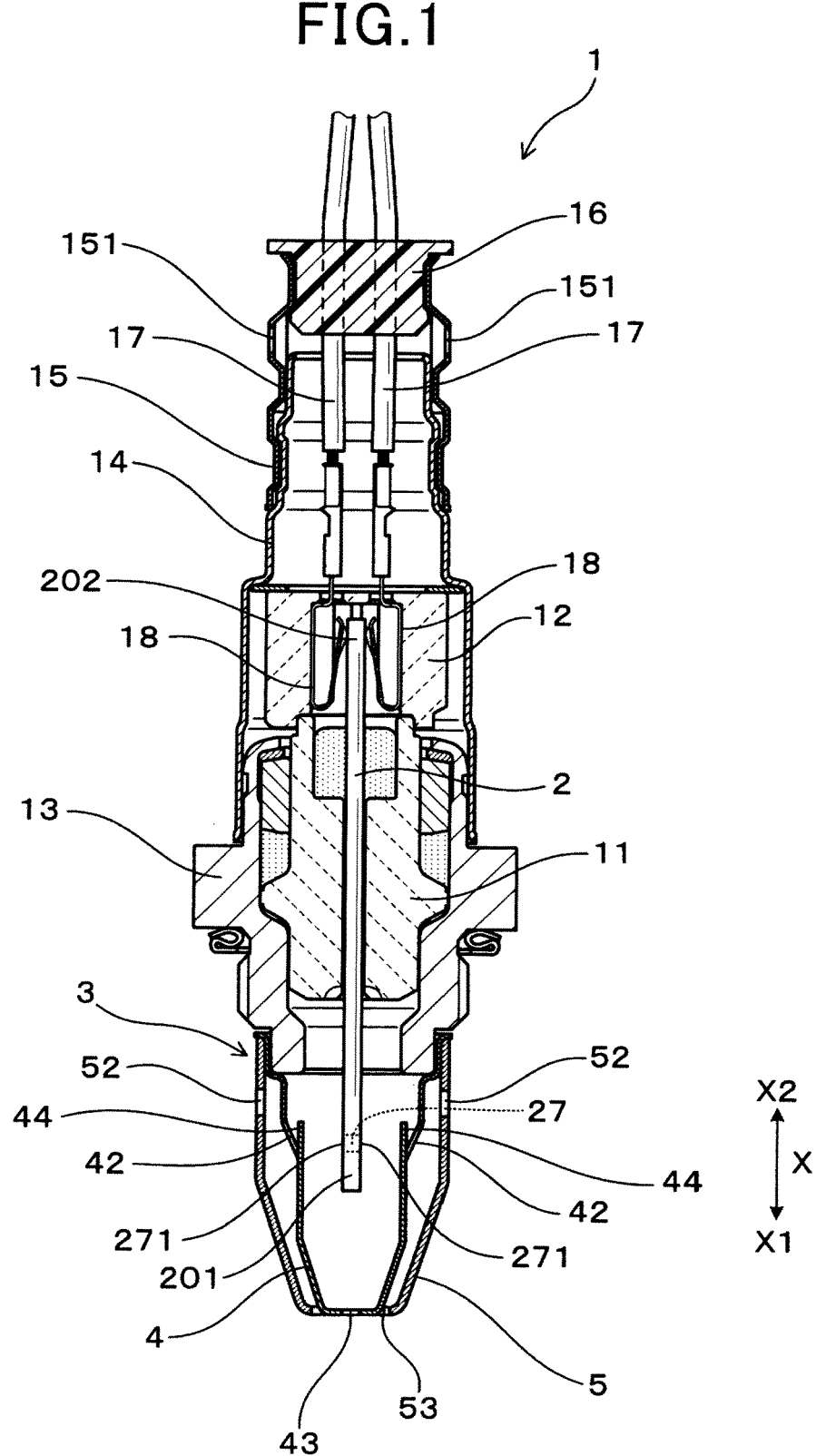
[FIG. 1] is a cross-sectional explanatory view showing the overall structure of a gas sensor in embodiment 1 of the invention.

In the above gas sensor, the term "axial distal end side" means one side of the axial direction of the gas sensor, or the side at which the gas sensor is exposed to the measurement gas. The term "axial proximal end side" means the side opposite to it.

The sensor element may be a stacked sensor element configured by stacking an oxygen ion conductive solid electrolyte body provided with a measurement gas-side electrode and a reference gas-side electrode, and porous diffusion resistance layer which allows the measurement gas to transmit therethrough to be in contact with the measurement gas-side electrode, for example. In the case of the above configuration, part of the diffusion resistance layer is exposed to the outer surface of the sensor element, and the exposed part serves as the above gas introduction part.

The gas introduction part may be provided at a plurality of positions in the distal end portion of the sensor element. A protection layer or the like for collecting poisoning components in the measurement gas may be provided on the outer surface of the sensor element so as to cover at least the exposed part (the gas introduction part) of the diffusion resistance layer.

The outer introduction opening may be provided plurally in the outer cover so as to stand circumferentially. The inner introduction opening may be provided plurally in the inner cover so as to stand circumferentially. The louver part of the inner cover is formed toward the axial proximal end side. Here, the words "formed toward the axial proximal end side" means that the direction in which the louver part is formed includes a component of the direction of the axial proximal end side. The louver part can be formed by extruding part of the inner cover inwardly by a mold or the like.

The louver opening degree, or the shortest distance between the part of the inner cover which is more to the axial proximal end side than the inner introduction opening is and the louver part may be smaller than or equal to 2.0 mm. In this case, since the flow rate of the measurement gas flowing into the inner cover from the inner introduction opening through the louver part can be controlled appropriately, it is possible to further increase the responsiveness for detecting the cylinder-to-cylinder imbalance.

If the louver opening degree exceeds 2.0 mm, it may become difficult to appropriately control the flow rate of the measurement gas flowing into the inner cover from the inner introduction opening through the louver part.

The axial intermediate position of the gas introduction part of the sensor element may be more to the axial proximal end side than the distal end portion of the louver part of the inner cover is. In this case, the measurement gas flowing into the inner cover from the inner introduction opening through the louver part can be caused to reach the gas introduction part of the sensor element rapidly through a short distance, to thereby further increase the responsiveness of the gas sensor. Incidentally, when the louver part of the inner cover is provided plurally, it is preferable that the axial intermediate position of the gas introduction part of the sensor element is more to the axial proximal end side than the distal end portions of all of the louver parts.

The axial distal end position of the gas introduction part of the sensor element may be more to the axial proximal end side than the distal end position of the louver part of the inner cover is. In this case, the measurement gas flowing into the inner cover from the inner introduction opening through the louver part can be caused to reach the gas introduction part of the sensor element rapidly through a short distance, to thereby further increase the responsiveness for detecting the cylinder-to-cylinder distance. When the louver part of the inner cover is provided plurally, it is preferable that the axial intermediate position of the gas introduction part of the sensor element is more to the axial proximal end side than the distal end portions of all of the louver parts are.

The inner introduction opening of the inner cover may be more to the axial distal end side or the axial proximal end side of the outer cover than the outer introduction opening of the outer cover is. Incidentally, the flood resistance can be increased more when the inner introduction opening is more to the axial distal end side than the outer introduction opening is. That is, the measurement gas introduced into the outer cover (between the outer cover and the inner cover) from the outer introduction opening flows to the axial distal end side, and flows into the inner cover from the inner introduction opening through the louver part. At this time, water drops flowing together with the measurement gas flows directly to the axial distal end side by their own weights. Accordingly, since the measurement gas and water drops can be separated easily, the effect of preventing water drops from entering the inner cover can be further increased. Hence, flooding of the sensor element and resultant breakage of the sensor element can be further prevented.

Embodiment 1

Figure 4:
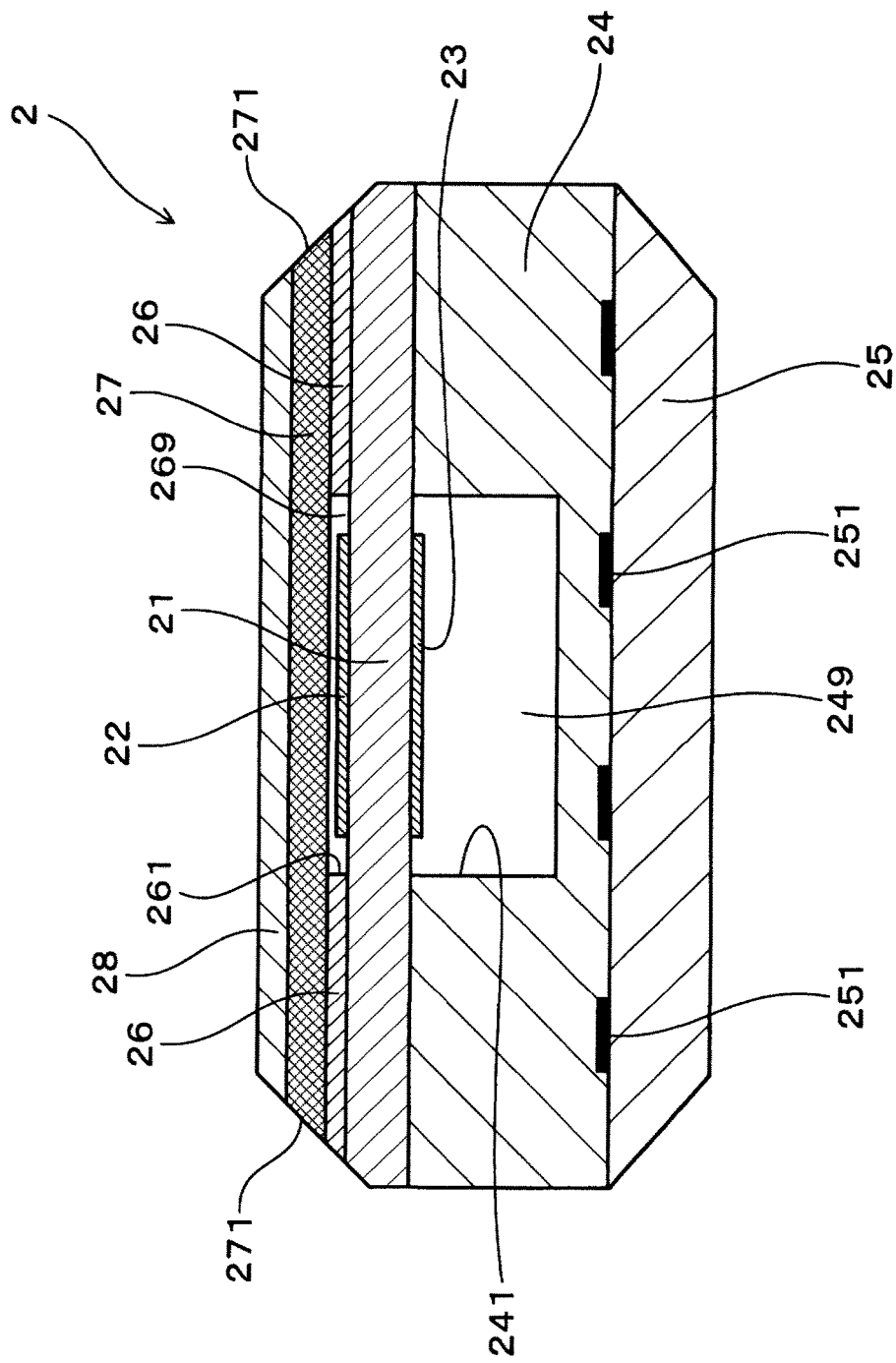
[FIG. 4] is a cross-sectional explanatory view showing the structure of a distal end portion of the sensor element in embodiment 1.

An embodiment of the gas sensor is explained with reference to drawings. As shown in FIGS. 1 and 4, the gas sensor 1 of this embodiment includes a sensor element 2 for detecting a specific gas concentration in a measurement gas, a housing 13 holding the sensor element 2 inserted therein, and an element cover 3 disposed at the axial distal end side X1 of the housing 13. The sensor element 2 is provided with gas introduction parts 271 for introducing the measurement gas thereinto at its distal end portion 201. The element cover 3 includes an inner cover 4 disposed so as to cover the distal end portion 201 of the sensor element 2 and an outer cover 5 disposed outside the inner cover 4.

Figure 2:
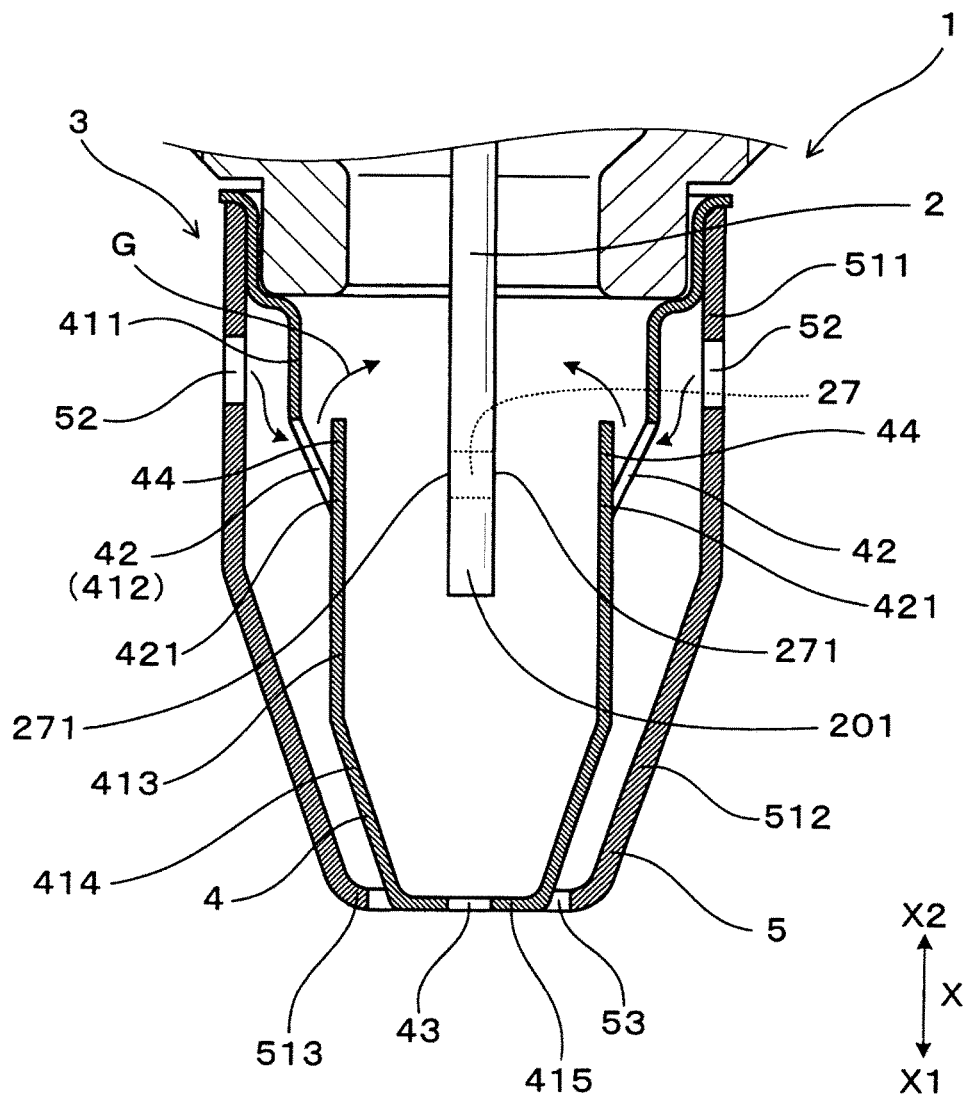
[FIG. 2] is a cross-sectional explanatory view showing the structure of an element cover of the gas sensor in embodiment 1.
Figure 3:
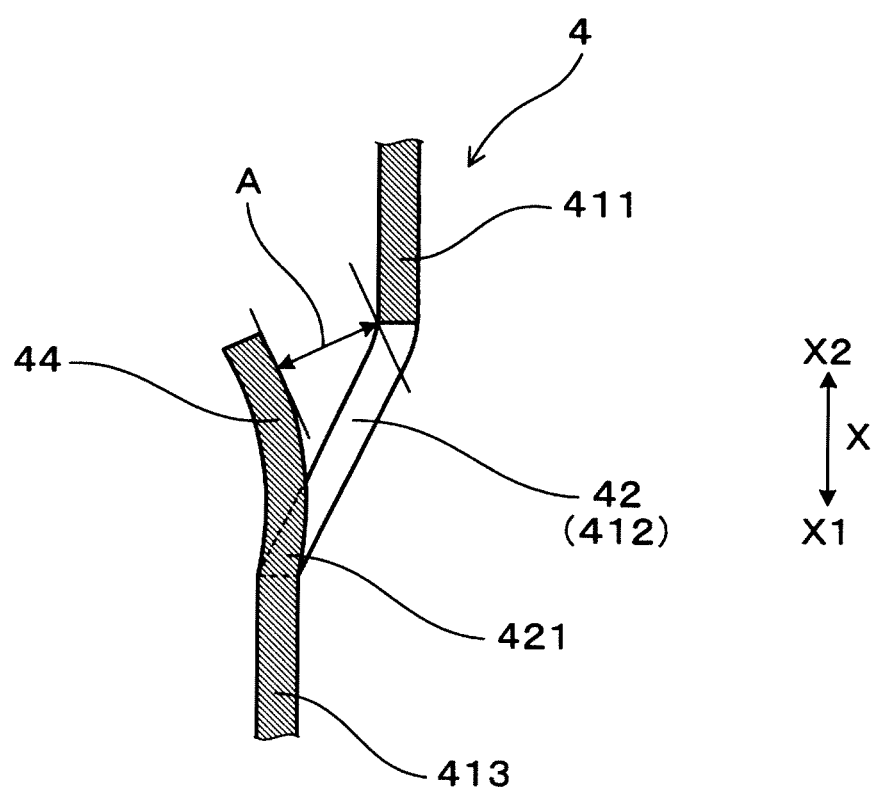
[FIG. 3] is a cross-sectional explanatory view showing an inner introduction opening and a louver part of an inner cover in embodiment 1.

As shown in FIGS. 2 and 3, the outer cover 5 is provided with outer introduction openings 52 for introducing the measurement gas into the outer cover 5. The inner cover 4 is provided with inner introduction openings 42 for introducing the measurement gas into the inner cover 4, and louver parts 44 each of which is folded from an end portion 421 at the axial distal end side X1 of the inner introduction opening 42 to the inside of the inner cover 4 and is formed toward the axial proximal end side X2.

Figure 5:
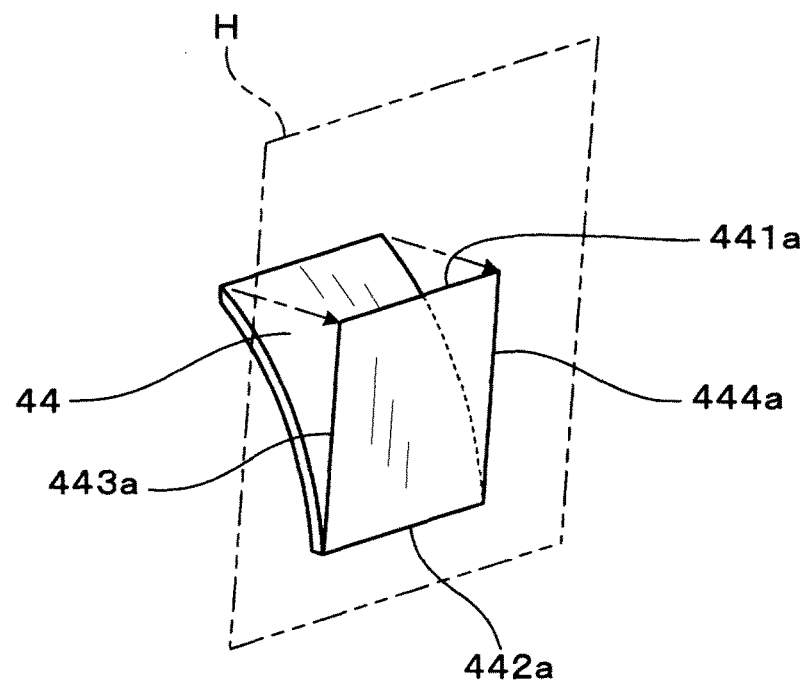
[FIG. 5] is an explanatory view showing the state in which the louver part is projected onto the same plane as the inner introduction opening in embodiment.
Figure 6:
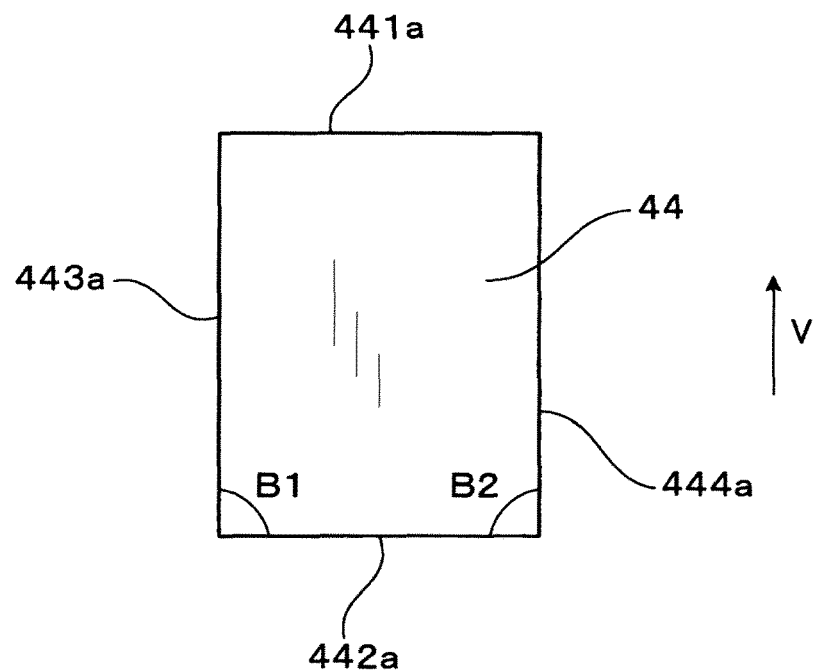
[FIG. 6] is an explanatory view showing the louver part projected onto the same plane as the inner introduction opening in embodiment 1.

As shown in FIGS. 5 and 6, when the louver part 44 is projected onto the same plane (plane H) as the inner introduction opening 42, a pair of lateral end edges 443a and 444a of the louver part 44 are formed in an approximately linear shape so as to be approximately parallel to the louver part forming direction V heading from the base side to the distal end side of the louver part 44. In the following, the gas sensor 1 of this embodiment is further explained in detail.

As shown in FIG. 1, in this embodiment, the words "axial distal end side X1" means one side of the axial direction X of the gas sensor 1, or the side at which the gas sensor 1 is exposed to the measurement gas. Further, the words "axial proximal end side X2" means the side opposite to it. As shown in this figure, in the gas sensor 1, the sensor element 2 of a plate-like shape is inserted into a first insulator 11 to be held. The first insulator 11 is held inside the housing 13.

As shown in FIG. 4, the sensor element 2 is an A/F sensor that detects the air-fuel ratio (A/F) of an air-fuel mixture supplied to an internal combustion engine based on the limiting current flowing between electrodes (later-described measurement gas-side electrode 22 and reference gas-side electrode 23) depending on the specific gas concentration (oxygen concentration) in the measurement gas (exhaust gas). FIG. 4 shows a cross section perpendicular to the axial direction X in the distal end portion 201 of the sensor element 2.

As shown in this figure, the sensor element 2 includes an oxygen ion conductive solid electrolyte body 21 consisting of zirconia. The solid electrolyte body 21, which is formed in a plate-like shape, is provided with a measurement gas-side electrode 22 to be exposed to the measurement gas at one surface thereof, and a reference gas-side electrode 23 to be exposed to a reference gas (the atmosphere in this embodiment).

As shown in this figure, a reference gas chamber layer 24 consisting of alumina is laminated on the side of the reference gas-side electrode 23 of the solid electrolyte body 21. The reference gas chamber layer 24 is provided with a groove part 241 by which a reference gas chamber 249 is formed. The reference gas chamber 249 is configured to be capable of introducing the reference gas.

A heater substrate 25 is laminated on the surface on the side opposite to the solid electrolyte body 21 of the reference gas chamber layer 24. The heater substrate 25 is provided with a heat generating body (heater) 251 which generates heat by being supplied with current, which faces the reference gas chamber layer 24. The heat generating body 251 is configured to be capable of heating the sensor element 2 to the activation temperature by generating heat when supplied with current.

As shown in this figure, an insulating layer 26 consisting of alumina is laminated on the side of the measurement gas-side electrode 22 of the solid electrolyte body 21. The insulating layer 26 includes an opening 261. A porous diffusion resistance layer 27 consisting of an alumina porous body which allows the measurement gas to transmit is laminated on the surface on the side opposite to the solid electrolyte body 21 of the insulating layer 26. Part of the diffusion resistance layer 27 is exposed to the outer surface of the sensor element 2. These introduction parts 271 are formed at a plurality of positions in this exposed part.

A measurement gas chamber 269 is formed at a place covered by the solid electrolyte body 21, the insulating layer 26 and the diffusion resistance layer 27. The measurement gas chamber 269 is configured to be capable of introducing the measurement gas having transmitted through the diffusion resistance layer 27. A shielding layer 28 consisting of alumina is laminated on the surface on the side opposite to the insulating layer 26 of the diffusion resistance layer 27. Although omitted from illustration, a protection layer and the like for collecting poisoning components in the measurement gas is provided of the outer surface of the sensor element 2 so as to cover the exposed part (gas introduction part 271) of the diffusion resistance layer 27.

As shown in FIG. 1, a first proximal end side cover 14 is fixed to the axial proximal end side X2 of the housing 13 so as to cover the proximal end portion 202 of the sensor element 2, and a second proximal end side cover 15 is fixed to the axial proximal end side X2 of the first proximal end side cover 14. The second proximal end side cover 15 is provided with air holes 151 for introducing the atmosphere. A proximal end side opening part of the second proximal end side cover 15 is closed by a sealing member 16 made of a rubber bushing. Lead members 17 to be connected to the outside are provided so as to penetrate through the sealing member 16.

A second insulator 12 covering the proximal end portion 202 of the sensor element 2 is provided in the first proximal end side cover 14 at the axial proximal end side X2 of the first insulator 11. Metal terminals 18 connected to the lead members 17 are provided in the second insulator 12. The metal terminals 18 are in contact with the electrode terminals of the sensor element 2 for providing electrical continuity.

As shown in this figure, the element cover 3 for protecting the sensor element 2 is disposed on the distal end side of the housing 13. The element cover 3 includes the bottomed cylindrical inner cover 4 disposed so as to cover the distal end portion 201 of the sensor element 2 and the bottomed cylindrical outer cover 5 disposed outside the inner cover 4. The inner cover 4 is fixed to the distal end portion of the housing 13. The outer cover 5 is fixed to the proximal end portion of the inner cover 4.

As shown in FIG. 2, the outer cover 5 includes an outer lateral part 511 the diameter of which is substantially constant in the axial direction X, a tapered outer diameter-reducing part 512 the diameter of which decreases toward the axial distal end side X1, and an outer bottom part 513 closing the axial distal end side X1 in this order from the axial proximal end side X2. The outer lateral part 511 is provided with the outer introduction openings 52 at a predetermined interval in the circumferential direction. The outer bottom part 513 is provided with outer discharge opening 53.

As shown in this figure, the inner cover 4 includes a first inner lateral part 411 the diameter of which is substantially constant in the axial direction X, a tapered first inner diameter-reducing part 412 the diameter of which decreases toward the axial distal end side X1, a second inner lateral part 413 the diameter of which is substantially constant in the axial direction X, a tapered second inner diameter-reducing part 414 the diameter of which decreases toward the axial distal end side X1, and an inner bottom part 415 closing the axial distal end side X1 in this order from the axial proximal end side X2. The inner bottom part 415 is disposed on substantially the same plane as the outer bottom part 513 of the outer cover 5 within the outer discharge opening 53 of the outer bottom part 513.

The first inner diameter-reducing part 412 is provided with the inner introduction openings 42 at a predetermined interval in the circumferential direction. The inner introduction openings 42 are disposed on a concentric circle with respect to the center axis of the gas sensor 1 in a plane orthogonal to the axial direction X. That is, the axial positions of all the inner introduction openings 42 are the same. All the inner introduction openings are more to the axial distal end side X1 than the outer introduction openings 52 of the outer cover 5 are. All the inner introduction openings 42 have a louver shape. That is, the first inner diameter-reducing part 412 is provided with the louver part 44 at each of the positions at each of which the inner introduction openings 42 is provided. The inner bottom part 415 is provided with an inner discharge opening 43.

As shown in FIG. 3, the louver part 44 is folded from the end portion 421 at the axial distal end side X1 of the inner introduction opening 32 to the inside of the inner cover 4, and is formed toward the axial proximal end side X2. The louver part 44 is formed in a roughly square shape. The louver part 44 is formed by extruding part of the inner cover 4 inwardly by a mold or the like. The louver opening degree A, or the shortest distance between the part of the inner cover 4 which is more to the axial proximal end side X2 than the inner introduction opening 42 (the first inner lateral part 411 in this embodiment) is and the louver part 44 is set smaller than or equal to 2.0 mm.

As shown in FIGS. 5 and 6, when the louver part 44 is projected onto the same plane (plane H) as the inner introduction opening 42, the louver part 44 includes a distal end side edge 441a, a base side edge 442a and a pair of lateral end edges 443a and 444a. The pair of the lateral end edges 443a and 444a are formed in approximately parallel to the louver forming direction V and in a roughly linear shape. The angles B1 and B2 between the base side edge 442a and the pair of the lateral end edges 443a and 444a of the louver part 44 are 90 degrees. Incidentally, FIGS. 5 and 6 show the louver part 44 extracted from the inner cover 44.

Next, advantageous effects of the gas sensor 1 of this embodiment are explained. In the gas sensor 1 of this embodiment, the inner cover 4 is provided with the inner introduction openings 42 and the louver parts 44 each of which is folded from the end portion 421 at the axial distal end side X1 of the inner introduction opening 42 to the inside of the inner cover 4, and is formed toward the axial proximal end side X2. When the louver part 44 is projected onto the same plane as the inner introduction opening 42, the pair of the lateral end edges 443a and 444a are formed approximately parallel to the louver forming direction V and in a roughly linear shape (see FIGS. 5 and 6).

Figure 7:
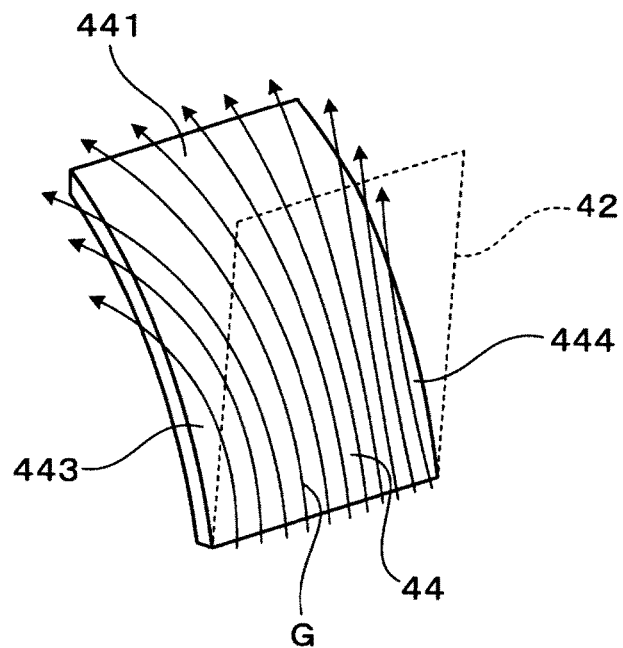
[FIG. 7] is an explanatory view showing flow of a measurement gas flowing into the inner cover from the inner introduction opening through the louver part in embodiment 1.

Accordingly, as shown in FIG. 7, when the measurement gas G introduced into the outer cover 5 (between the outer cover 5 and the inner cover 4) from the outer introduction openings 52 flows from the inner introduction opening parts 42 into the inner cover 4, the measurement gas G easily flows from the base side to the distal end side of the louver part 44 along the surface of the louver part 44. Further, it is possible to suppress part of the measurement gas G from leaking from the lateral end portions 443 and 444 of the louver part 44 to both sides, and flowing into the inner cover 4. That is, it is possible to increase the percentage of the flow amount of the measurement gas G flowing in through the distal end portion 441 of the louver part 44. Incidentally, FIG. 7, in which the louver part 44 is extracted from the inner cover 4, schematically shows flow of the measurement gas G flowing in from the inner introduction opening 42 (the dotted line part).

As a result, the measurement gas G can be caused to flow from the inner introduction opening 42 in a desired direction within the inner cover 4 through the louver part 44, so that the measurement gas G can be caused to reach the gas introduction part 271 of the sensor element 2 rapidly through a distance as short as possible. Further, it is possible to cause the measurement gas G to reach the gas introduction parts 271 of the sensor element 2 without mixing it with a measurement gas G which has flowed in through another inner introduction opening 42. The measurement gases G discharged from the respective cylinders of the internal combustion engine are caused to reach the gas introduction parts 271 of the sensor element 2 in succession, and are suppressed from mixing with one another before reaching the gas introduction parts 271 of the sensor element 2.

As a result, the responsiveness of the gas sensor 1 can be increased, and change of the output value (the air-fuel ratio: A/F) of the gas sensor 1 used as an index of the cylinder-to-cylinder imbalance of the internal combustion engine can be detected more correctly. Thus, the detection accuracy of the cylinder-to-cylinder imbalance of the internal combustion engine in the gas sensor 1 can be increased.

Figure 8:
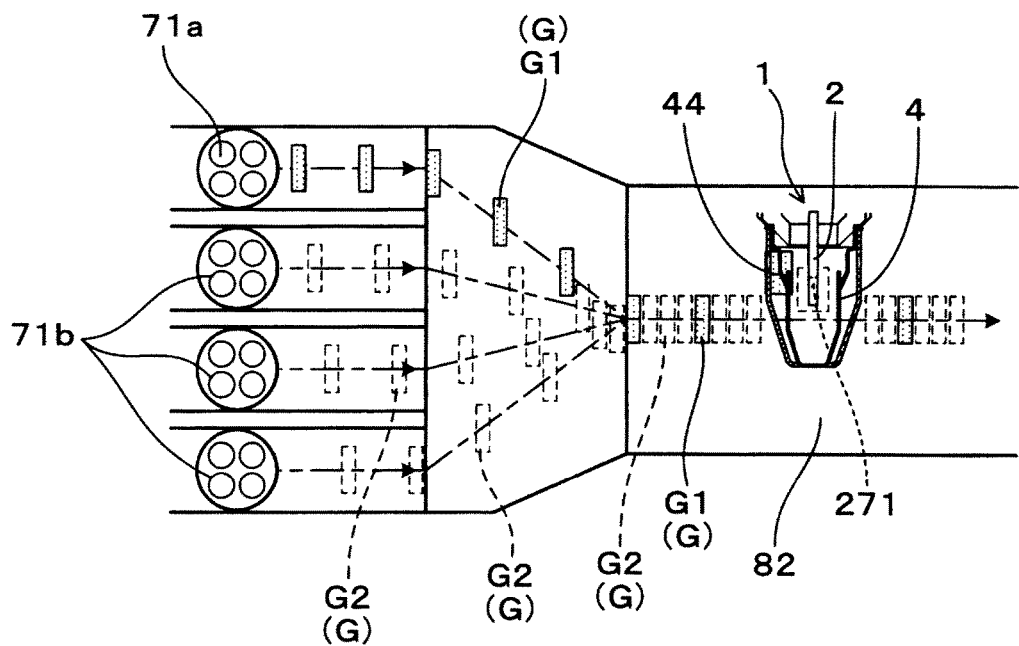
[FIG. 8] is an explanatory view showing flow of the measurement gas in a multi-cylinder internal combustion engine in embodiment 1.
Figure 9:
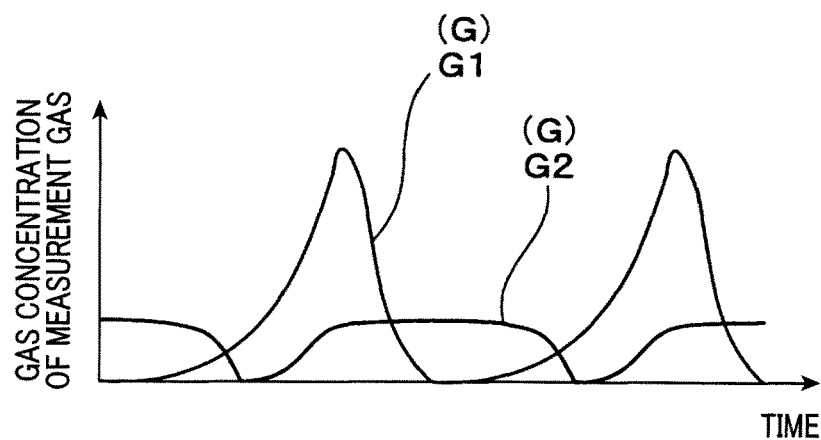
[FIG. 9] is a graph showing variation with time of gas concentration of the measurement gas with the horizontal axis representing time and the horizontal axis representing the gas concentration.

FIG. 8 shows flow of the measurement gas G (exhaust gas) in the exhaust pipe 82 of the multi-cylinder internal combustion engine when the air-fuel ratio of any one cylinder 71a is on the rich side with respective to the theoretical air-fuel ratio, and the air-fuel ratio of any other cylinder 71b is on the lean side with respect to the theoretical air-fuel ratio. As shown in this figure, dischargings from the respective cylinders 71a and 71b are performed in succession. The measurement gas G1 on the rich side and the measurement gas G2 on the lean side reach the gas sensor 1 within the exhaust pipe 82 in succession. FIG. 9 shows variation with time of the gas concentration in the measurement gas G measured by the gas sensor 1. As shown in this figure, in the gas sensor 1, the measurement gas G1 on the rich side and the measurement gas G2 on the lean side are measured alternately. Since the measurement gases G which are discharged one after another and flow into the inner cover 4 one after another are in the state of being difficult to mix with each other, it is possible to prevent the measurement gas G1 on the rich side and the measurement gas G2 on the lean side reaching with a predetermined time interval therebetween from mixing with each other.

Figure 10:
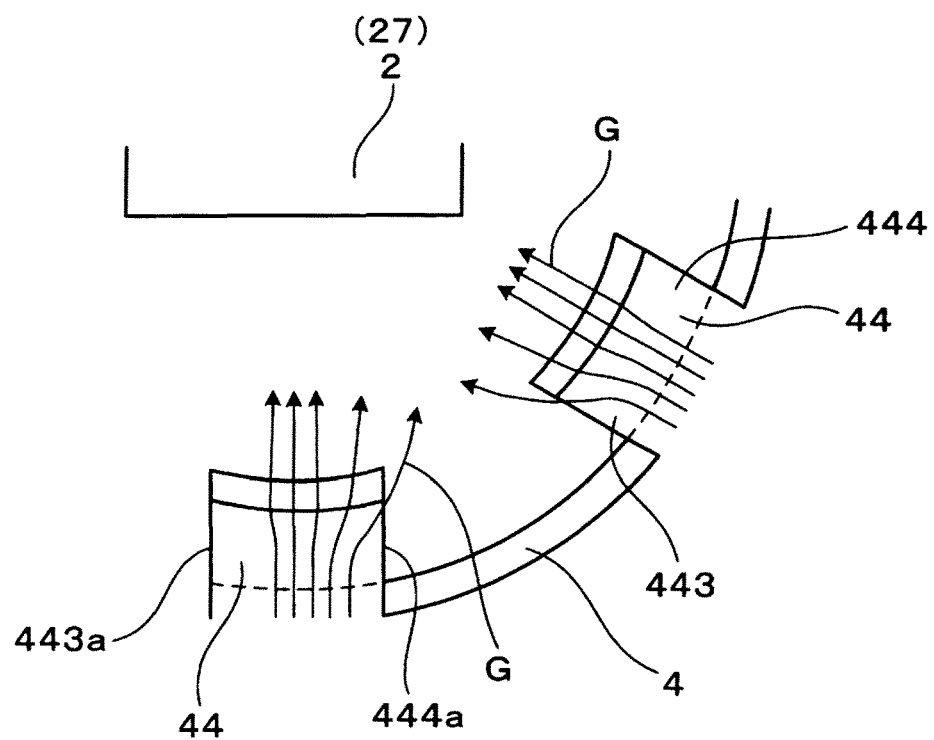
[FIG. 10] is an explanatory view showing the louver part in the inner cover as viewed in the axial direction of the gas sensor in embodiment 1.

FIG. 10 shows the state where the louver part 44 in the inner cover 4 is formed plurally in the circumferential direction of the inner cover 4. The pair of the lateral end edges 443a and 444a of the louver part 44 are formed approximately parallel to the louver forming direction heading from the base side to the distal end side of the louver part 44 and in a roughly linear shape. In this embodiment, most of the measurement gas G flows from the base side to the distal end side of the louver part 44. Accordingly, it is possible to suppress part of the measurement gas G from leaking from the lateral end portions 443 and 444 of the louver part 44 to both sides, and to suppress the measurement gases G flowing through the adjacent louver parts 44 from mixing with each other.

Figure 11:
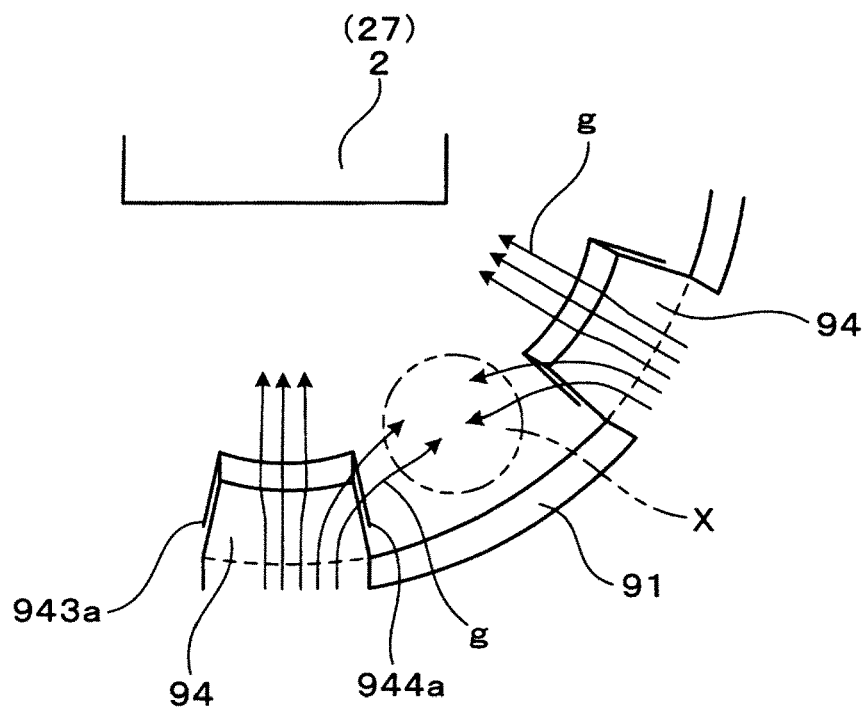
[FIG. 11] is an explanatory view showing a louver part of an inner cover in the background art as viewed in the axial direction of a gas sensor.

On the other hand, FIG. 11 shows, as a comparative example, a case where the pair of the lateral end edges 943a and 944a of the louver part 94 are formed inclined inwardly relative to the louver forming direction heading from the base side to the distal end side of the louver part 94. As shown in this figure, in the case of this louver part 94 being provided, the measurement gases g flowing through the adjacent louver parts 94 mix with each other, and a stagnation of the measurement gases g (shown by the two-point chain line in this figure) occurs. Further, the measurement gas g flowing into the inner cover 91 earlier and the measurement gas g flowing into the inner cover 91 later become likely to mix with each other. As shown in FIG. 10, since the louver part 44 is formed to have the above described shape, it is possible to suppress the measurement gases G discharged one after another from mixing with each other, to thereby increase the detection accuracy of the cylinder-to-cylinder imbalance of the internal combustion engine in the gas sensor 1.

In this example, the louver opening degree A, or the shortest distance between the part of the inner cover 4 which is more to the axial proximal end side X2 (the first inner lateral part 411) than the inner introduction opening 42 is and the louver part 44 is smaller than or equal to 2.0 mm. Accordingly, it is possible to appropriately control the flow rate of the measurement gas G flowing into the inner cover 4 from the inner introduction opening 42 through the louver part 44, and to further increase the responsiveness of the gas sensor 1.

The inner introduction opening 42 of the inner cover 4 is more to the axial distal end side X1 than the outer introduction opening 52 of the outer cover 5 is. Accordingly, the measurement gas G introduced into the outer cover 5 (between the outer cover 5 and the inner cover 4) from the outer introduction opening 52 flows to the axial distal end side X1, and flows into the inner cover 4 from the inner introduction opening 42 through the louver part 44. At this time, water drops flowing together with the measurement gas G flows directly to the axial distal end side X1 by their own weights. Accordingly, since the measurement gas G and water drops can be separated easily, the effect of preventing water drops from entering the inner cover 4 can be further increased. Further, flooding of the sensor element 2 and resultant breakage of the sensor element 2 can be further prevented. Incidentally, the separated water drops are discharged to the outside from the outer discharge opening 53 of the outer cover 5.

As described above, according to this example, the gas sensor 1 which is capable of increasing the detection accuracy of the cylinder-to-cylinder imbalance of an internal combustion engine, and is excellent in the responsiveness for detecting the cylinder-to-cylinder imbalance can be provided.

Figure 12:
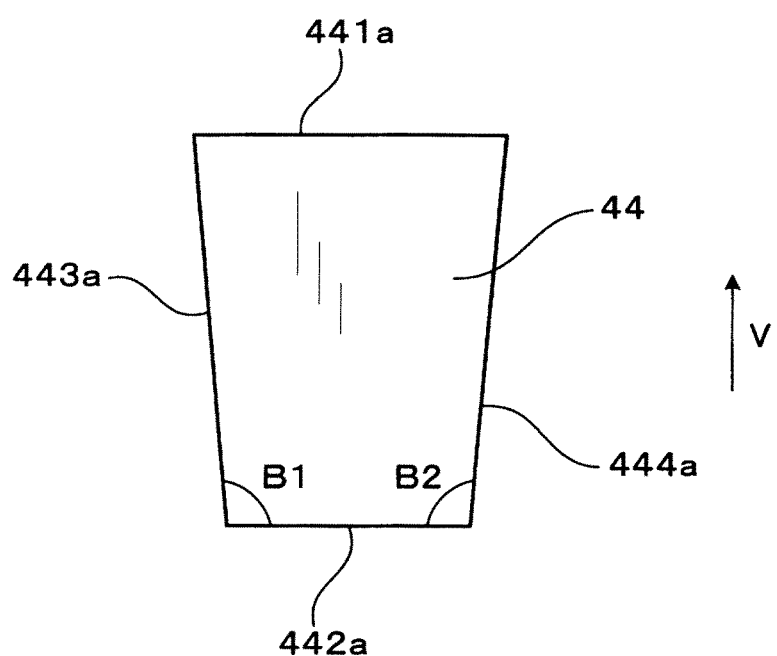
[FIG. 12] is an explanatory view showing a louver part of a different example, which is projected onto the same plane as the inner introduction opening in embodiment 1.

Incidentally, in this example, as shown in FIGS. 5 and 6, when the louver part 44 is projected onto the same plane as the inner introduction opening 42, the pair of the lateral end edges 443a and 444a of the louver part 44 are formed in approximately parallel to the louver forming direction V and in a roughly linear shape. However, the pair of the lateral end edges 443a nad 444a of the louver part 44 may be formed inclined outwardly to the louver forming direction V and in a roughly linear shape as shown in FIG. 12, for example. That is, the angles B1 and B2 between the base side edge 442a and the pair of the lateral end edges 443a and 444a of the louver part 44 may be larger than 90 degrees (larger than 90 degrees and smaller than 95 degrees, for example).

Figure 13:
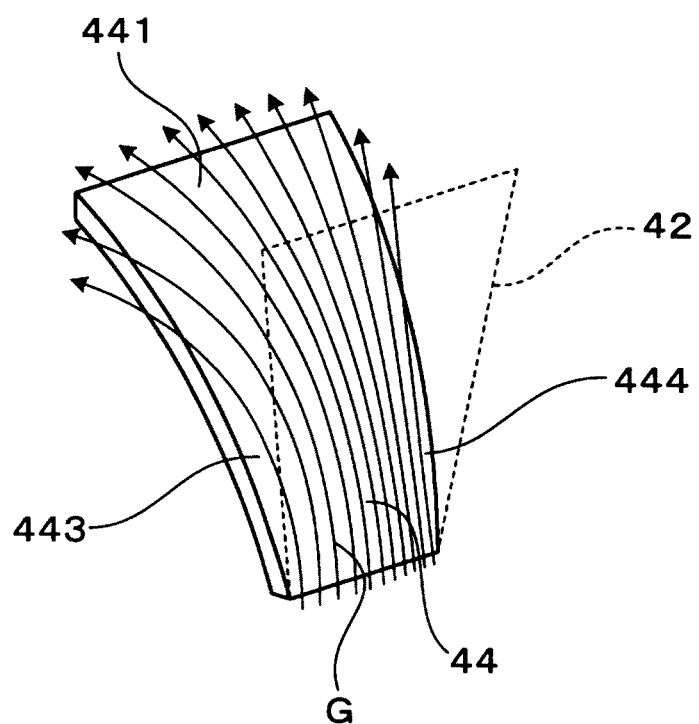
[FIG. 13] is an explanatory view showing flow of the measurement gas flowing into the inner cover from the inner introduction opening through the louver part of the different example in embodiment 1.

In this configuration, the measurement gas G flows more easily from the base side to the distal end side of the louver part 44 along the surface of the louver part 44, as shown in FIG. 13. Accordingly, it is possible to further suppress part of the measurement gas G from leaking from the lateral end portions 443 and 444 of the louver part 44 and flowing into the inner cover 4. That is, it is possible to increase the percentage of the flow amount of the measurement gas G flowing in through the distal end portion 441 of the louver part 44.

Embodiment 2

Figure 14:
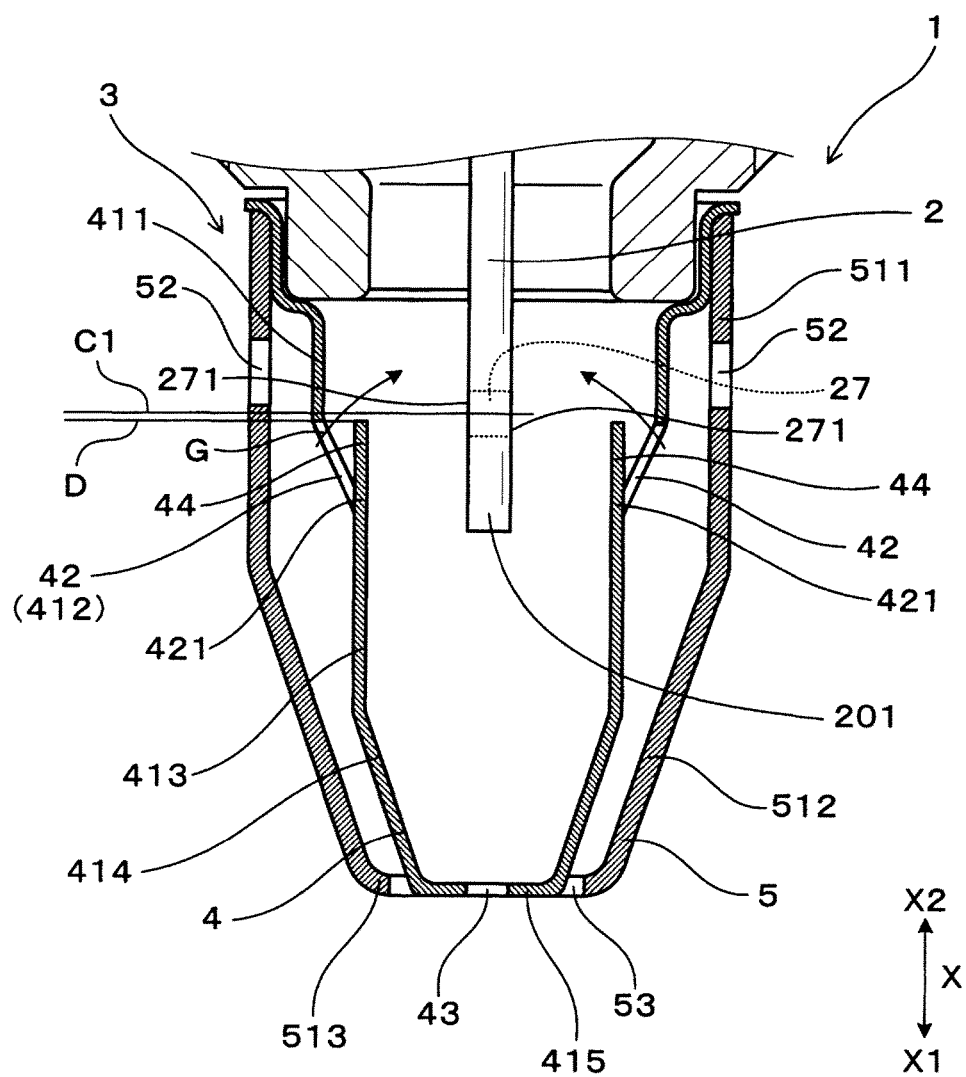
[FIG. 14] is a cross-sectional explanatory view showing an example of the structure of an element cover of a gas sensor in embodiment 2 of the invention.
Figure 15:
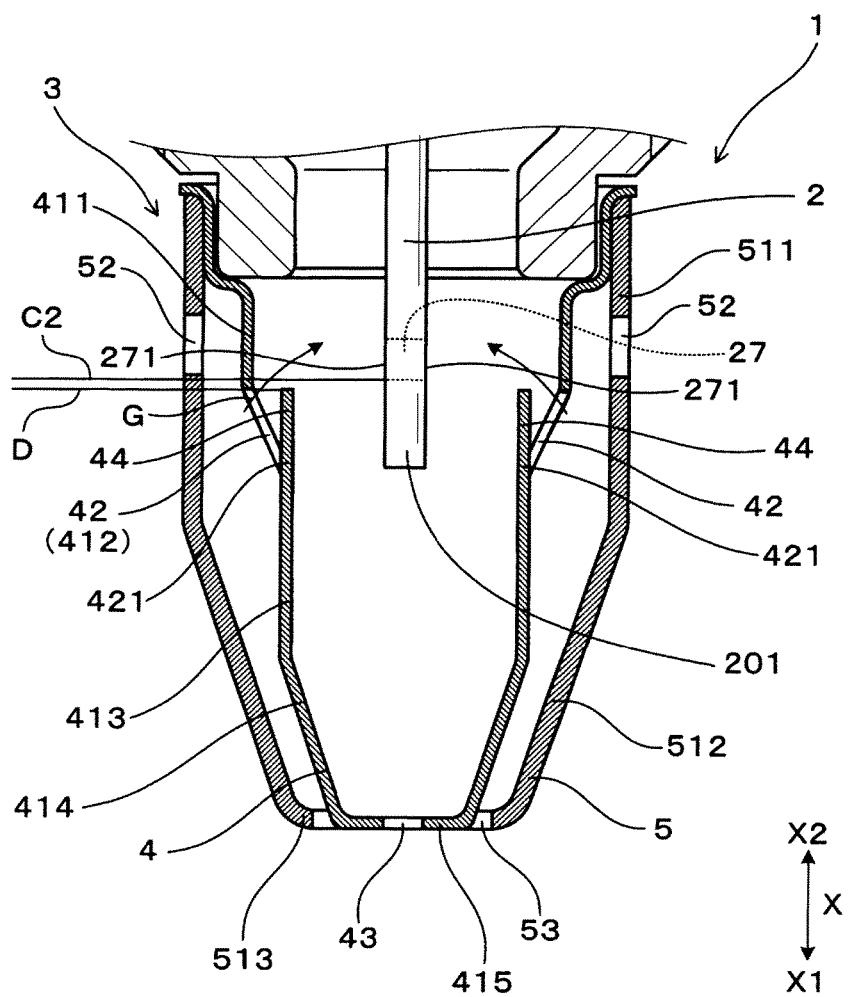
[FIG. 15] is a cross-sectional explanatory view showing an example of the structure of the element cover of the gas sensor in embodiment 2.

As shown in FIGS. 14 and 15, this embodiment is an example in which the positional relationship between the louver part 44 of the inner cover 4 and the gas introduction parts 271 of the sensor element 2 is changed. As shown in FIG. 14, the axial intermediate position C1 of the gas introduction parts 271 of the sensor element 2 is more to the axial proximal end side X2 than the distal end position D of the louver part 44 of the inner cover 4 is. In this example, it is more to the axial proximal end side X2 than the distal end positions D of all the louver parts 44 is.

As shown in FIG. 15, the axial distal end position C2 of the gas introduction parts 271 of the sensor element 2 is more to the axial proximal end side X2 than the distal end position D of the louver part 44 of the inner cover 4 is. In this example, the axial distal end position C2 of the gas introduction parts 271 of the sensor element 2 is more to the axial proximal end side X2 than the distal end positions D of all the louver parts 44 of the inner cover 4 is. In either example, the other basic structure is the same as embodiment 1. The same structures as embodiment 1 are followed by the same signs, and explanations thereof are omitted In this embodiment, most of the measurement gas G which is about to flow into the inner cover 4 from the inner introduction opening 42 can be caused to flow to the axial proximal end side X2 by the louver part 44 of the inner cover 4. Further, since the axial intermediate position C1 of the gas introduction parts 271 is more to the axial proximal end side X2 than the axial proximal end position D1 of the inner introduction openings 42 is, the measurement gas G introduced into the inner cover 4 from the inner introduction openings 42 can be caused to reach the gas introduction parts 271 of the sensor element 2 rapidly through a distance as short as possible. The responsiveness of the gas sensor 1 for detecting the cylinder-to-cylinder imbalance can be further increased. The other basic advantageous effects are the same as embodiment 1.

Embodiment 3

This embodiment is for evaluating the detection accuracy of the cylinder-to-cylinder imbalance for the gas sensor of the present invention. In this embodiment, a gas sensor of the present invention having the similar structure to that shown in FIG. 14 of embodiment 2 was prepared. That is, as shown in FIGS. 5 and 6, when the louver part 44 is projected onto the same plane (plane H) as the inner introduction opening 42, the pair of the lateral end edges 443a and 444a of the louver part 44 are formed in approximately parallel to the louver forming direction V and in a roughly linear shape. The angles B1 and B2 between the base side edge 442a and the pair of the lateral end edges 443a and 444a of the louver part 44 are 90 degrees.

Figure 19:
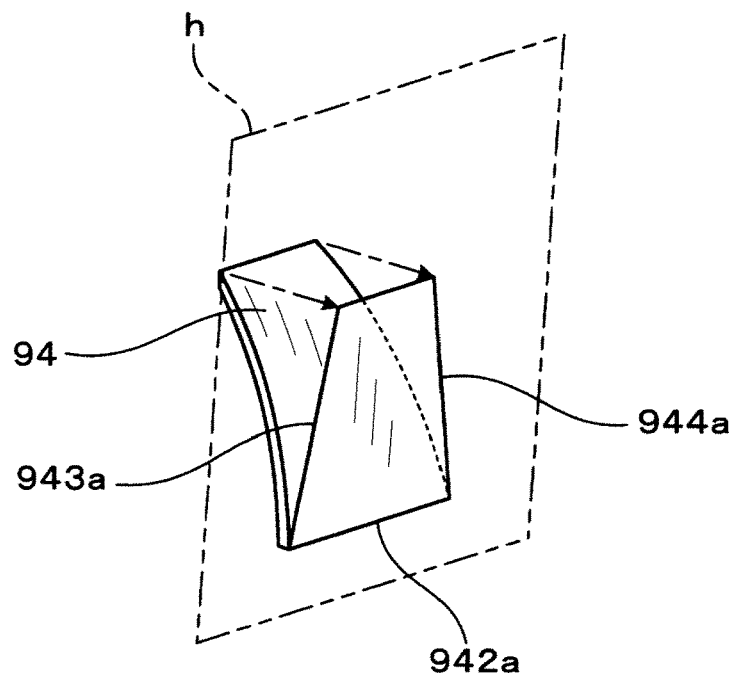
[FIG. 19] is an explanatory view showing a state in which the louver part is projected onto the same plane as the inner introduction opening in the background art.
Figure 20:
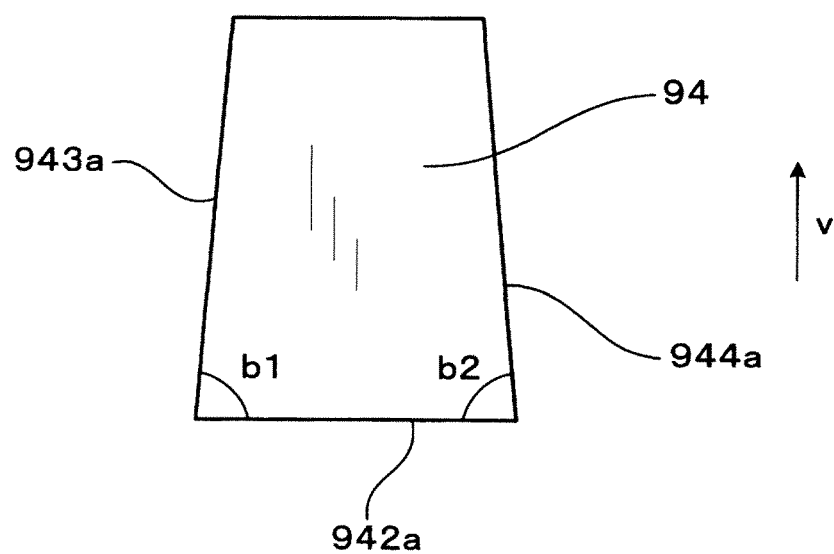
[FIG. 20] is an explanatory view showing the louver part projected onto the same plane as the inner introduction opening in the background art.
Figure 21:
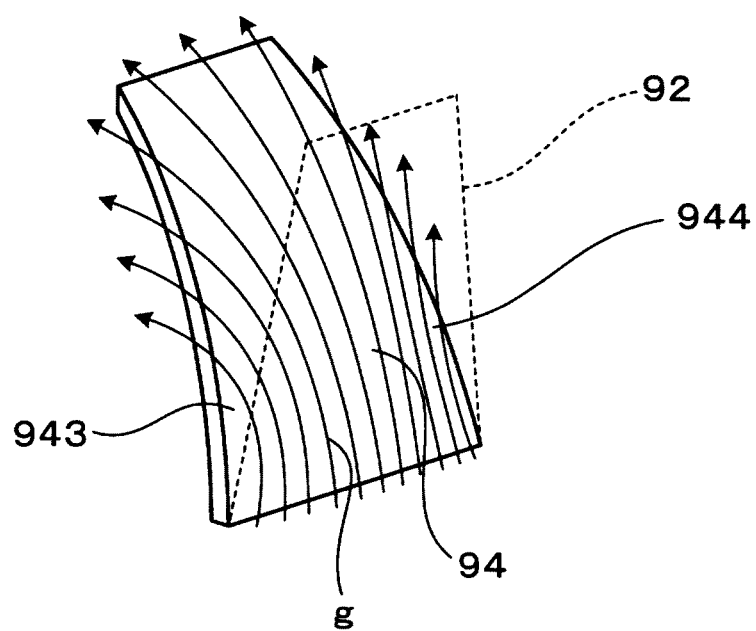
[FIG. 21] is an explanatory view showing flow of a measurement gas flowing into the inner cover from the inner introduction opening through the louver part in the background art.

Further, in this embodiment, a gas sensor having the conventional structure was prepared as a comparative product. That is, as shown in FIGS. 19 and 20, when the louver part 94 is projected onto the same plane (plane h) as the inner introduction opening 92, the pair of the lateral end edges 943a and 944a of the louver part 94 are formed inclined inwardly to the louver forming direction v and in a roughly linear shape. The angles b1 and b2 between the base side end edge 942a and the pair of the side end edges 943a and 944a of the louver part 94 are smaller than 90 degrees (specifically, 86 degrees).

Figure 16:
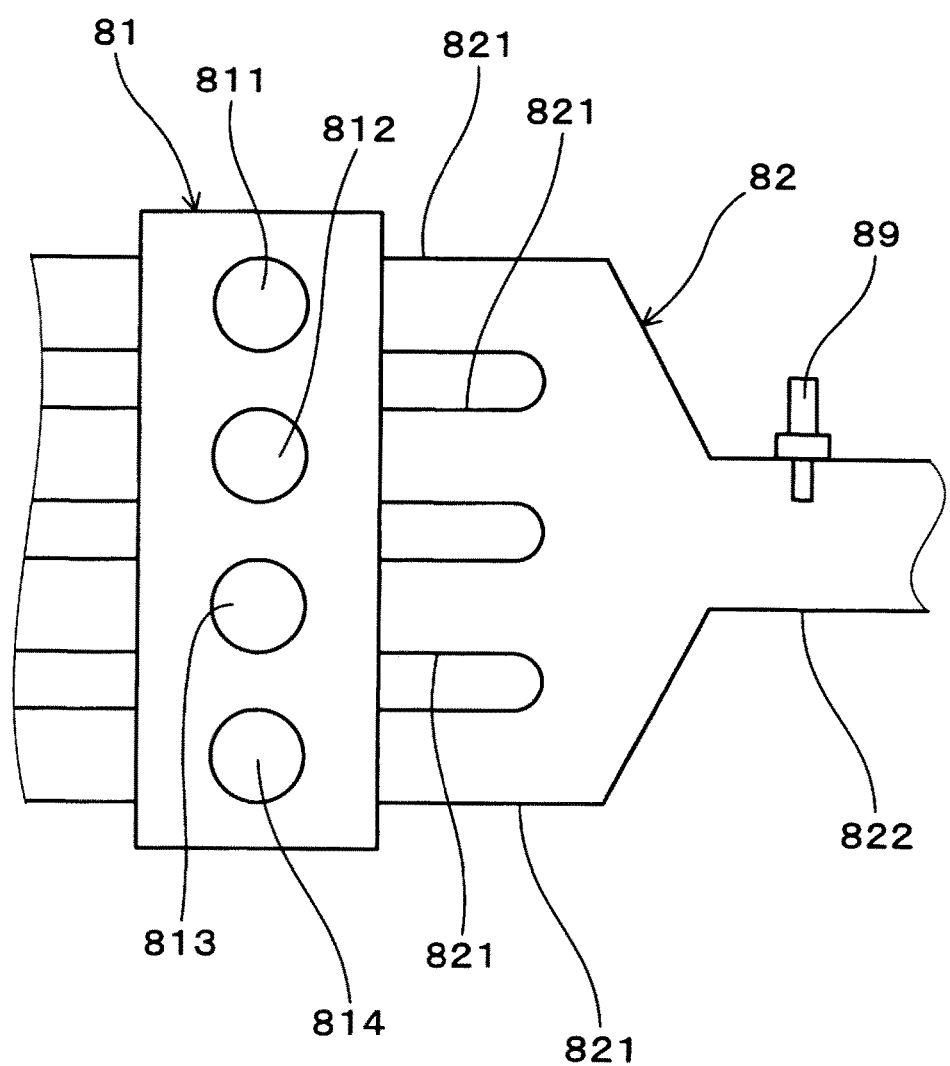
[FIG. 16] is an explanatory view showing an exhaust pipe of an internal combustion engine provided with a gas sensor in embodiment 3 of the invention.

Next, an evaluation method of the cylinder-to-cylinder imbalance of an internal combustion engine is explained. In this embodiment, as shown in FIG. 16, an in-line four cylinder internal combustion engine 81 including four cylinders (a first cylinder 811, a second cylinder 812, a third cylinder 813 and a fourth cylinder 814) was prepared. The respective cylinders 811 to 814 of the internal combustion engine 81 are in communication with exhaust branch parts 821 of the exhaust pipe 82, respectively. The four exhaust branch parts 821 are gathered on their downstream side to be in communication with an exhaust collecting part 822 of the exhaust pipe 82. A gas sensor 89 was mounted on the exhaust collecting part 822 of this exhaust pipe 82.

Thereafter, the internal combustion engine was driven under a predetermined condition. In this embodiment, the rotational speed was set to 1600 rpm, and the gas flow rate per unit cross-sectional area within the exhaust pipe was set to 20 g/s. Of the four cylinders, the fuel injection amount of the second cylinder was increased excessively compared to the other cylinders. In this embodiment, the setting was such that the air-fuel ratio of the second cylinder is in the state of being shifted to the rich side (the state where the fuel injection amount is increased by 40%).

Figure 17:
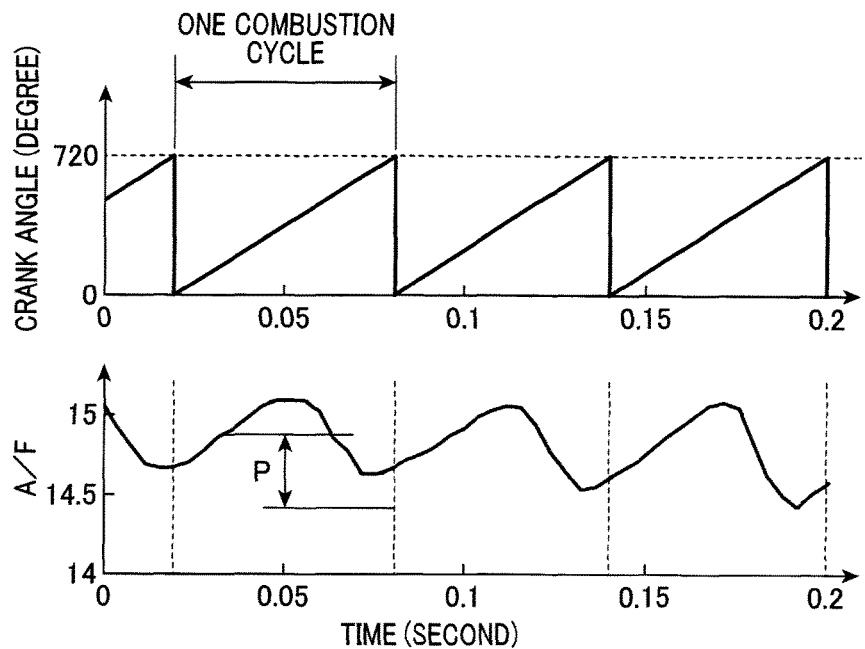
[FIG. 17] is a graph showing variations with time of the crank angle and A/F in embodiment 3.

Then, as shown in FIG. 17, the output value (the air-fuel ratio: A/F) of the gas sensor was obtained with a lapse of time. Here, the waveform of the output value of the gas sensor varies with a combustion cycle of the internal combustion engine as a cycle thereof. One combustion cycle of the internal combustion engine is started when the crank angle is 0 degrees, and is ended when the crank angle is 720 degrees. During one combustion cycle, combustion is performed in the order of the first cylinder, third cylinder, fourth cylinder and second cylinder. During one combustion cycle, discharge is performed in the order of the second cylinder, first cylinder, third cylinder and fourth cylinder because discharge is performed after combustion is performed in the respective cylinders. Accordingly, ideally, the exhaust gases discharged from the respective cylinders reach the sensor element of the gas sensor in the order of the second cylinder, first cylinder, third cylinder and fourth cylinder.

Next, the evaluation method of the cylinder-to-cylinder imbalance is explained. As shown in FIG. 17, an amplitude P (difference between the maximum value and the minimum value) of the waveform in one combustion cycle was obtained from the obtained output values (air-fuel ratio: A/F) as an imbalance response value. In this embodiment, the thirteen pieces of the gas sensors were prepared for each of the present invention and the comparative product, and the above imbalance response value and its average value was obtained for each of them. Subsequently, the imbalance response value ratio (%) of the present invention with respect to an average value of the imbalance response values of the comparative products as a reference (=100%) was obtained. Higher value of the imbalance response value ratio represents higher detecting accuracy of the cylinder-to-cylinder imbalance of the internal combustion engine.

Figure 18:
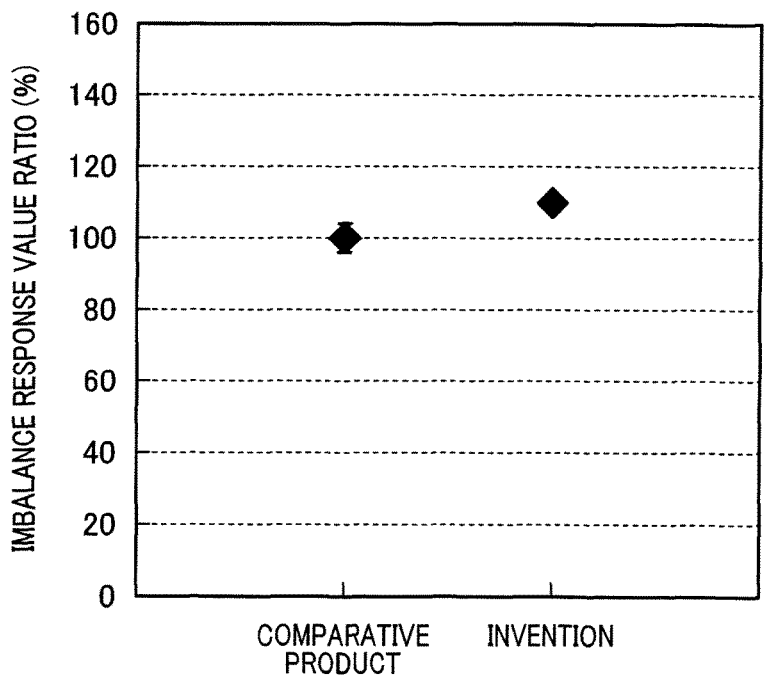
[FIG. 18] is a graph showing imbalance response value ratios of the invention in embodiment 3 and a comparative product.

FIG. 18 shows evaluation results of the detection accuracy of the cylinder-to-cylinder imbalance of the internal combustion engine. The vertical axis of this figure represents the imbalance response value ratio (%). In this figure, averages of the imbalance response value ratios are plotted. Also, variations (maximum value, minimum value) of the imbalance response value ratios are shown. These variations of the imbalance response value ratios were obtained eliminating variations of the engine rotational speed, the intake air amount, the exhaust gas temperature and so on so that only the variation of the shape of the louver part 94 or 96 is reflected as much as possible. From this figure, it was found that the gas sensor of the present invention is approximately 12% higher in the imbalance response value ratio than the gas sensor of the comparative product. That is, it was found that, when the cylinder-to-cylinder imbalance of an internal combustion engine is the same, the gas sensor of the present invention can detect this cylinder-to-cylinder imbalance with a higher degree of accuracy.

From the above results, it was found that the gas sensor of the present invention can increase the detection accuracy of the cylinder-to-cylinder imbalance of an internal combustion engine, and is excellent in the responsiveness for detecting the cylinder-to-cylinder imbalance.

EXPLANATION OF SYMBOLS

1 Gas sensor
13 Housing
2 Sensor element
210 Distal end portion (distal end of sensor element)
271 Gas introduction part
3 Element cover
4 Inner cover
42 Inner introduction opening
421 Distal end portion (distal end portion at axial distal end side of inner introduction opening)
44 Louver part
443a, 444a lateral end edge (lateral end edge of the louver part)
5 Outer cover
52 Outer introduction opening
X1 Axial distal end side
X2 Axial proximal end side
V Louver forming direction

The invention claimed is:

1. A gas sensor comprising:
a sensor element for detecting a specific gas concentration in a measurement gas;
a housing holding the sensor element inserted therein; and
an element cover disposed at an axial distal end side of the housing; wherein
a gas introduction part is provided in a distal end portion of the sensor element for introducing therein the measurement gas,
the element cover includes an inner cover disposed so as to cover the distal end portion of the sensor element and an outer cover disposed outside the inner cover,
the outer cover is provided with an outer introduction opening for introducing the measurement gas into the outer cover,
the inner cover is provided with an inner introduction opening for introducing the measurement gas into the inner cover, and a louver part which is folded from an end portion at the axial distal end side of the inner introduction opening to the inside of the inner cover and is formed toward an axial proximal end side, the inner introduction opening being opened to the axial proximal end side of the louver part and also opened to circumferential sides of the louver part, and
when the louver part is projected onto a same plane as the inner introduction opening, a pair of lateral end edges of the louver part are formed in an approximately linear shape so as to be approximately parallel to a louver part forming direction heading from a base side to a distal end side of the louver part.

2. The gas sensor according to claim 1, wherein
a louver opening degree, or a shortest distance between a part of the inner cover which is more to the axial proximal end side than the inner introduction opening is and the louver part is smaller than or equal to 2.0 mm.

3. The gas sensor according to claim 1, wherein
an axial intermediate position of the gas introduction part of the sensor element is more to the axial proximal end side than a distal end position of the louver part of the inner cover is.

4. The gas sensor according to claim 1, wherein
an axial distal end position of the gas introduction part of the sensor element is more to the axial proximal end side than a distal end position of the louver part of the inner cover is.

5. A gas sensor comprising:
a sensor element for detecting a specific gas concentration in a measurement gas;
a housing holding the sensor element inserted therein; and
an element cover disposed at an axial distal end side of the housing; wherein
a gas introduction part is provided in a distal end portion of the sensor element for introducing therein the measurement gas,
the element cover includes an inner cover disposed so as to cover the distal end portion of the sensor element and an outer cover disposed outside the inner cover,
the outer cover is provided with an outer introduction opening for introducing the measurement gas into the outer cover,
the inner cover is provided with an inner introduction opening for introducing the measurement gas into the inner cover, and a louver part which is folded from an end portion at the axial distal end side of the inner introduction opening to the inside of the inner cover and is formed toward an axial proximal end side, the inner introduction opening being opened to the axial proximal end side of the louver part and also opened to circumferential sides of the louver part, and when the louver part is projected onto a same plane as the inner introduction opening, a pair of lateral end edges of the louver part are formed in an approximately linear shape so as to be inclined outwardly to a louver part forming direction heading from a base side to a distal end side of the louver part.

6. The gas sensor according to claim 5, wherein
a louver opening degree, or a shortest distance between a part of the inner cover which is more to the axial proximal end side than the inner introduction opening is and the louver part is smaller than or equal to 2.0 mm.

7. The gas sensor according to claim 5, wherein
an axial intermediate position of the gas introduction part of the sensor element is more to the axial proximal end side than a distal end position of the louver part of the inner cover is.

8. The gas sensor according to claim 5, wherein
an axial distal end position of the gas introduction part of the sensor element is more to the axial proximal end side than a distal end position of the louver part of the inner cover is.

* * * * *